United States Patent [19]

Goolsby et al.

[11] 4,419,892
[45] Dec. 13, 1983

[54] METHOD FOR DETERMINATION OF INTERNAL PIPELINE OR TUBING CORROSION

[75] Inventors: Alvin D. Goolsby, Houston, Tex.; Ignatius A. M. Hesselman, Amsterdam, Netherlands

[73] Assignee: Shell Oil Company, Houston, Tex.

[21] Appl. No.: 284,280

[22] Filed: Jul. 17, 1981

[30] Foreign Application Priority Data

Sep. 3, 1980 [GB] United Kingdom ............... 8028446

[51] Int. Cl.³ .................. G01M 19/00; G01N 33/00; G01N 17/00
[52] U.S. Cl. .................................. 73/432 R; 73/49.5; 422/53
[58] Field of Search ............ 73/49.5, 49.6, 37.9, 73/432 G, 86, 105, 9, 49.1, 37.5; 422/53

[56] References Cited

U.S. PATENT DOCUMENTS

| | | | |
|---|---|---|---|
| 2,266,566 | 12/1941 | Poole | 73/49.5 X |
| 3,793,875 | 2/1974 | Jurkiewicz | 73/37.9 X |
| 3,903,730 | 9/1975 | Mathews, Jr. et al. | 73/49.1 X |
| 3,916,673 | 11/1975 | Gass et al. | 73/49.5 X |
| 3,973,441 | 8/1976 | Porter | 73/432 G |
| 4,000,655 | 1/1977 | Jones | 73/432 G |
| 4,342,225 | 8/1982 | Jandea et al. | 73/432 G |
| 4,367,646 | 1/1983 | Allen, Sr. et al. | 73/37.9 |

FOREIGN PATENT DOCUMENTS 838385  6/1981  U.S.S.R. ............................ 73/49.5

Primary Examiner—S. Clement Swisher
Assistant Examiner—Tom Noland

[57] ABSTRACT

A method for determining the variations of the internal condition of a pipeline or tubing, by propelling a pig, which is sealed against the pipeline or tubing wall, through the pipeline by means of a constant flowing driving fluid comprising the steps of continuously measuring and recording the pressure of the driving fluid or the pressure differential across the pig during pigging of the pipeline or tubing and deriving from the recorded pressure signals a plurality of quantities representative for the pressure variations in selected successive intervals of the pipeline or tubing, each interval having a predetermined length, in such a way that the total length of the pipeline or tubing to be inspected is covered, and comparing the values of the quantities thus obtained with reference data of these quantities, and deriving from comparision information as to the internal diameter variations of the pipeline or tubing being inspected.

4 Claims, 5 Drawing Figures

COEFFICIENTS OF FRICTION BETWEEN PIG AND INTERNAL PIPELINE WALL

RECORDED PRESSURE DATA
COVERING 160 m OF PIPELINE

REFERENCE DATA SHOWING
CORRESPONDENCE BETWEEN
PRESSURE DATA AND DIAMETER
OF PIPELINE

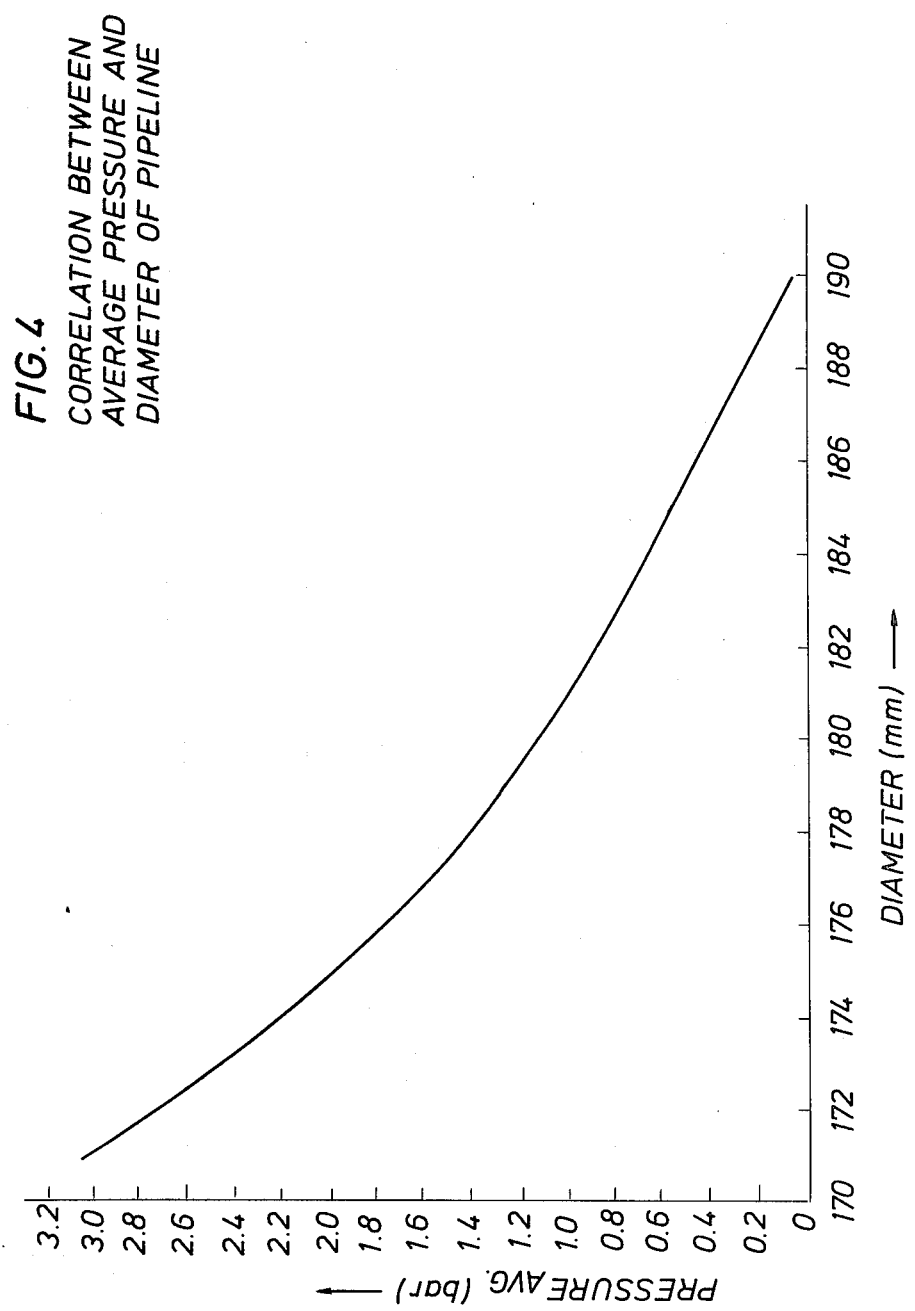

METHOD FOR DETERMINATION OF INTERNAL PIPELINE OR TUBING CORROSION

BACKGROUND OF THE INVENTION

The steel wall of a pipeline or tubing may be subject to internal corrosion. This is dependent, obviously, on the matter that is transported through the pipeline or tubing. Both liquids and gases may attack the steel wall.

Two forms of corrosion may be of interest, namely uniform corrosion and pitting. In the case of uniform corrosion the wall thickness decreases more or less uniformly and it will be clear that this could lead to the pipeline becoming unserviceable, because the wall will become too weak to resist the internal pressure. Pitting could lead to leakage and this phenomenon must also be avoided.

It is obviously of great importance to be regularly informed about the state of the pipeline or tubing to be able to take measures in time.

Since downtime is costly, the inspection of pipelines or tubings should preferably be carried out during operation. Moreover, pipelines or tubings are often installed where access is difficult, e.g., underground or under water, so that methods of internal inspection are to be preferred.

It is known that internal pipeline or tubing corrosion may be determined from the internal dimensions of the pipeline or tubing obtained by means of a pig adapted to be carried along by the flow of matter through the pipeline or tubing. Such a pig is fitted with an array of probes protruding outward from the pig and springload to press against the inner wall of the pipeline or tubing in a radial direction.

The probes are fitted with displacement pick-ups and the pig is further equipped with apparatus for processing the signals from the displacement pick-ups and for recording the results of such processing.

The pig is further fitted with means for the determination of distance. This may be a time clock, whose signal is regularly recorded and may be used in conjunction with the flow velocity to determine the locations of recordings. It is also possible to use a supporting wheel whose revolutions indicate the location of a recording. In this way the location of uniform corrosion and pitting can be determined quantitatively.

However, such a pig provided with an array or probes is less suitable for use in pipes having a small diameter. Such small pipes are often used, e.g., in heat-exchangers, flow lines, etc.

Further, it is at time sufficient to obtain only qualitative information about the condition of the pipe wall without the need of an expensive instrumented pig and a time-consuming processing of signals.

SUMMARY OF THE INVENTION

The present invention relates to a method for the determination of internal pipeline or tubing corrosion. In particular, the invention relates to a method for determining variations of the internal dimensions of a pipeline or tubing.

It is therefore an object of the present invention to provide a method for determining internal corrosion of a pipeline or tubing, which method provides information as to the internal condition of the pipe wall in a relatively simple and cheap way.

Further, it is an object of the present invention to provide a method for obtaining information about the internal condition of a pipeline or tubing, which method can be used qualitatively as well as quantitatively.

It is another object of the present invention to provide a method for obtaining information about the internal pipeline or tubing condition, which method can be used in pipes having a relatively small diameter as well as in pipes having a larger diameter.

The invention therefore relates to a method for determining the variations of the internal condition of a pipeline or tubing wall, through the pipeline or tubing by means of a constant flowing driving fluid comprising the steps of continuously measuring and recording the pressure of the said driving fluid or the pressure differential across the pig during pigging of the pipeline or tubing and deriving from the recorded pressure signals a plurality of quantities representative for the pressure variations in selected successive intervals of the pipeline or tubing, each interval having a predetermined length, in such a way that the total length of the pipeline or tubing to be inspected is covered, and comparing the values of the quantities thus obtained with reference data of these quantities, and deriving from said comparison information as to the internal diameter variations of the pipeline or tubing being inspected. As already indicated above, the method according to the invention is in particular applicable to pipes having a small diameter and a relatively short length, for example up to a few kilometers.

DESCRIPTION OF THE DRAWINGS

The present invention will now be described by way of example in more detail with reference to the drawings, in which:

FIG. 4 shows a reference graph, representing a correlation between the average pressure and the diameter of the pipeline.

DESCRIPTION OF PREFERRED EMBODIMENTS

Figure 1:
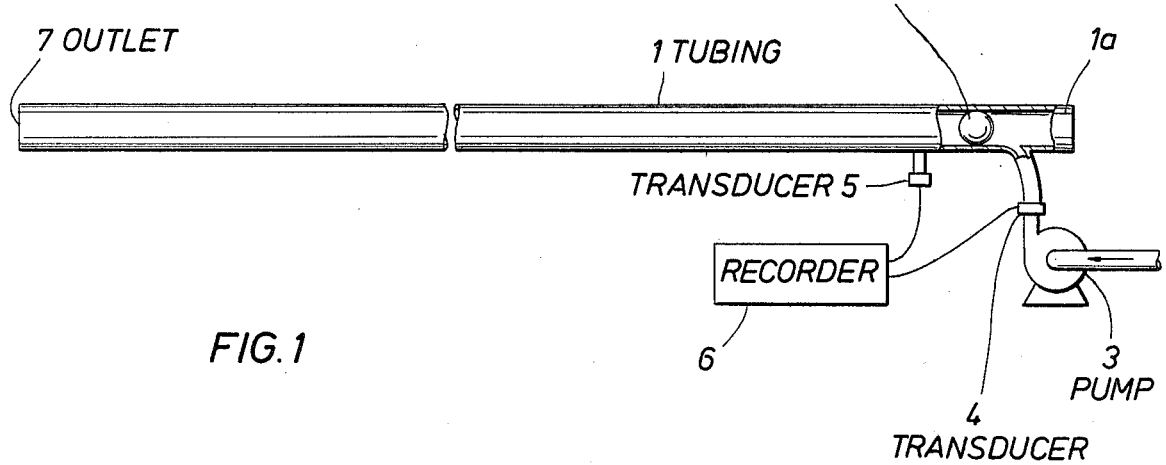
FIG. 1 shows schematically an example of carrying out the method of the invention.

In the following description the use of the term "pipeline" is intended to include also the term "tubing". Further, the said method according to the invention may be applicable as an addition to the above mentioned known pigging methods to provide a rough indication of the pipe wall condition. The method according to the invention is in particular applicable for a qualitative survey and localization of regions of high corrosion.

The invention is based upon the fact that a correlation between the pressure recording obtained during pigging and the internal diameter of the pipeline exists. It will be clear for those skilled in the art, that a good sealing between pig and pipe wall should exist to prevent leakage.

Using this fact continuous pressure recording during pipeline pigging is a means for evaluating the internal corrosion condition of the line, a decrease of the pressure of the driving fluid or the pressure differential across the pig indicating an increase of the pipeline diameter due to corrosion. The information as to the pipeline wall condition may be obtained in several ways. One of the possibilities is that the fluid pressure used to propel the pig through the pipeline or the pressure differential across the pig is continuously measured and recorded during each of several pig trips. The recorded fluctuations in pressure as obtained on a specific trip may be considered as a "finger print" which may be used as reference data for trips which are carried out subsequently. In this way a qualitative indication as to the condition of the pipe wall may be obtained. Such a qualitative indication may be sufficient in many cases, if the pipeline is not too old.

Another way of using the correlation between pressure recording and the diameter of the pipe is obtaining a set of reference data from which the desired diameter data of the pipe to be inspected can be derived, by determining and recording reference data belonging to predetermined various known segments of the pipeline. This can for example, be done by known devices, which measure and record the internal pipeline diameter. The pressure can be continuously measured and recorded by any means suitable for the purpose. For example a pig, provided with mechanical means may be used to measure and record the pipeline data. Of course any other device suitable for the purpose may be used. In this way a one-to-one correspondence between a determined pressure value or any suitable representation of the measured pressure variations in a predetermined pipe length, and a determined diameter value is obtained. Such a representation may be the average pressure in the pipeline, which can be derived from the measured pressure variations. Representing the reference data thus obtained may for example take place graphically. It will be clear to those skilled in the art that the form of such a reference graph will depend on the shape of the pig and the coefficient of friction between the pig and internal pipeline wall. So a set of different reference curves should be obtained.

In an advantageous embodiment of the invention the measured pressure values recorded during a run of the pig are compared with the reference data by means of a microprocessor. However, the said comparison may also be carried out graphically.

It will be appreciated that measuring and recording the pressure values may be carried out in several ways.

For example, the pig may be provided with any instrument suitable for the purpose to carry out the said pressure measurements and recordings. Also a non-instrumented pig may be used, in which case the pressure measurements and recordings may be done at any place of the pipeline suitable for the purpose.

According to an advantageous embodiment of the invention a pig is used, said pig mechanically being adapted in such a way, that the said pig measures the pressure differential between opposite locations on said pig in order to perform localized pressure measurements. The said pig may rotate about the axial line of symmetry of the pipeline.

Referring now to FIG. 1, an example of carrying out the method of the invention is shown.

In a pipeline or tubing 1 a pig 2 is launched at a suitable inlet 1(a). The pig is propelled through the pipeline by any suitable fluid by means of a pump 3. The fluid flow is measured by a flow transducer 4. The pressure is continuously measured by a pressure transducer 5. The measured pressure and flow signals are recorded on any suitable recorder means 6, which is connected by a suitable line with the said transducers 4 and 5. The pig 2 is received after its journey through the pipeline 1 at an outlet 7 of the pipeline or tubing. The instantaneous net volume flow of fluid is used to calculate the approximate location of the pig at all times and thus to correlate pressure data with location. Fluid leakage past the pig may introduce uncertainty in the calculated position, but may be corrected in a suitable way, for example as follows: the difference between the integrated volume of fluid used to propel the pig a known distance and the pipe volume swept by the pig in the same distance is the leakage volume. The leakage volume divided by the swept volume is the fractional error in calculated position at any point, and may be applied as a correction factor. Further refinements may be possible, such as off-line correction for localized leakage past the pig based on a predetermined algorithm between pipe inner diameter and leak rate. Known artifacts in the pipe, such as welds, tees and valves will produce characteristic pressure pulses, which may serve as bench marks for position referencing.

Figure 2:
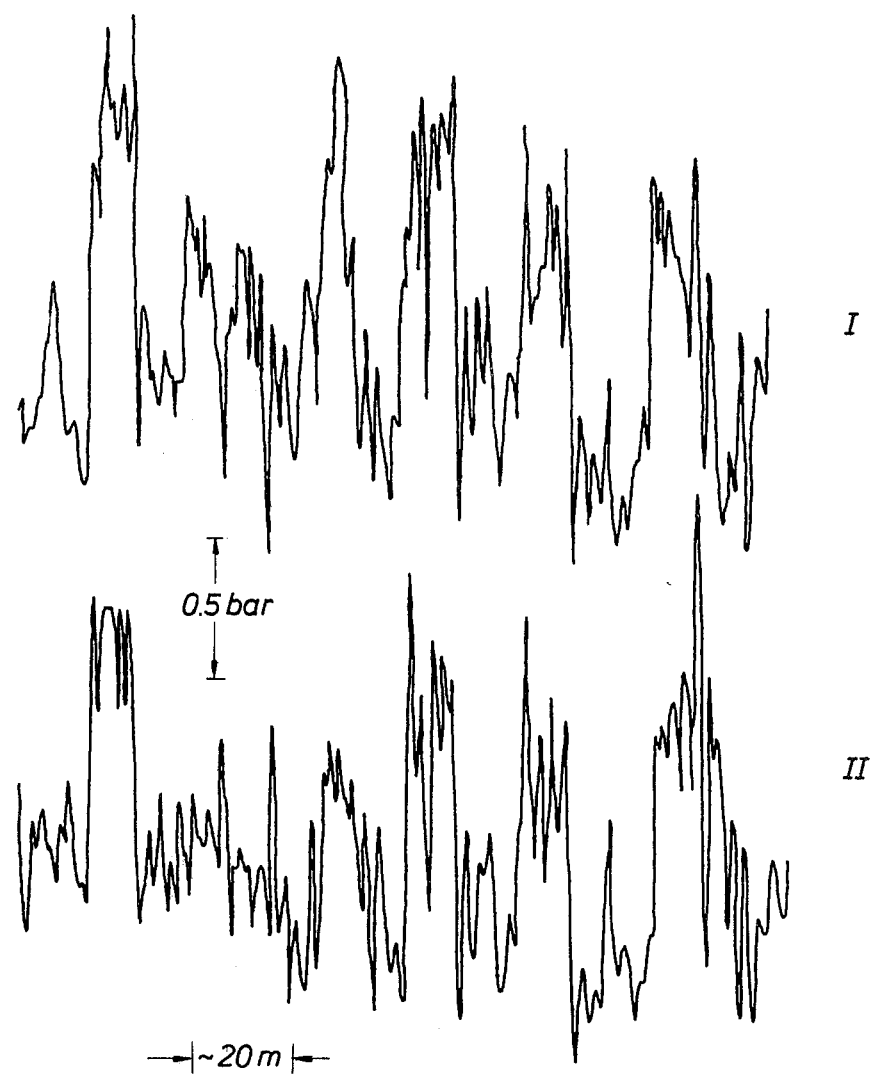
FIG. 2 shows examples of recorded pressure data by a recording means covering a distance of 160 m of the pipeline.

FIG. 2 shows examples of pressure data as recorded by the recording means during pigging, covering a distance of 160 m of the pipeline. Along the horizontal axis the distance from the inlet of the pipeline (in meters) is represented, whereas the vertical axis represents the recorded pressure (in bar) in the pipeline. The reference numbers I and II represent serial runs. Run I may for example be considered as a "finger print" for Run II which is carried out a certain point of time after Run I.

Comparison of Runs I and II provides an indication as to the change of internal condition of the part of the pipeline being inspected.

Figure 3:
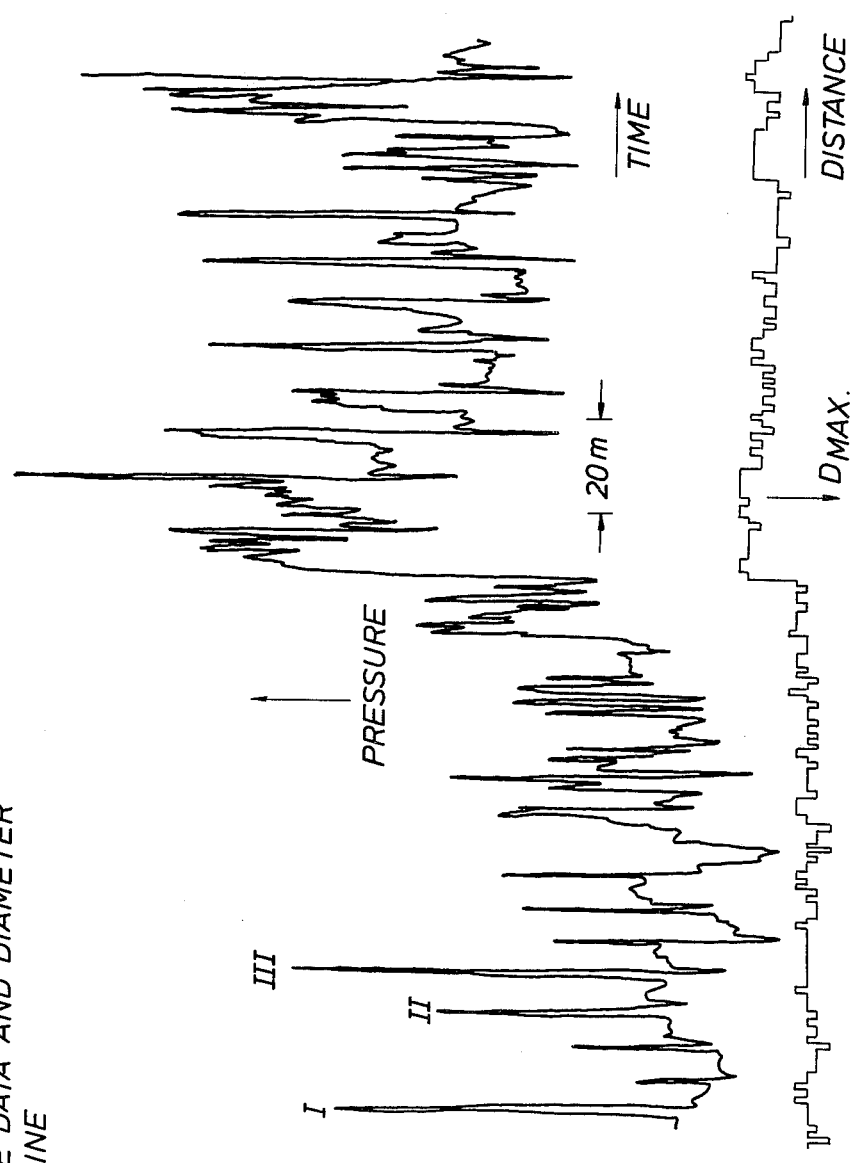
FIG. 3 shows an example of a record of reference data, said record shows a one-to-one correspondence between the recorded pressure data and the measured diameter of the pipeline.

FIG. 3 shows an example of the recorded pressure data and measured diameter data, which are used to obtain reference data using a one-to-one correspondence between pressure and diameter values.

In FIG. 3 along the two horizontal axes the time in relation to distance from the inlet are represented, whereas the upper vertical axis represents the pressure (in bar). The large spikes I, II and III in FIG. 3 are due to weld material protruding into the pipe.

The lower horizontal axis represents the distance from the inlet, whereas the lower vertical axis represents the measured diameter D max. of the pipeline. As already mentioned in the above, reference data are obtained by launching a suitable pig into the pipeline and by measuring and recording the diameter data and pressure data. It appears that a one-to-one correspondence between the recorded pressure data and diameter data exists.

FIG. 4 shows a reference graph representing a correlation between the average pressure in the pipeline values and diameter values. Water was used as propelling medium in an 8-inch pipeline of 2 km length. The horizontal axis represents the diameter D max. in mm, whereas the vertical axis represents the average pressure p av. (in bar). A pipeline distance of 200 m was covered and p av. was taken over pipeline intervals of 4 meters.

The origin in this figure is:
p=0 bar
D=190 mm

Figure 5:
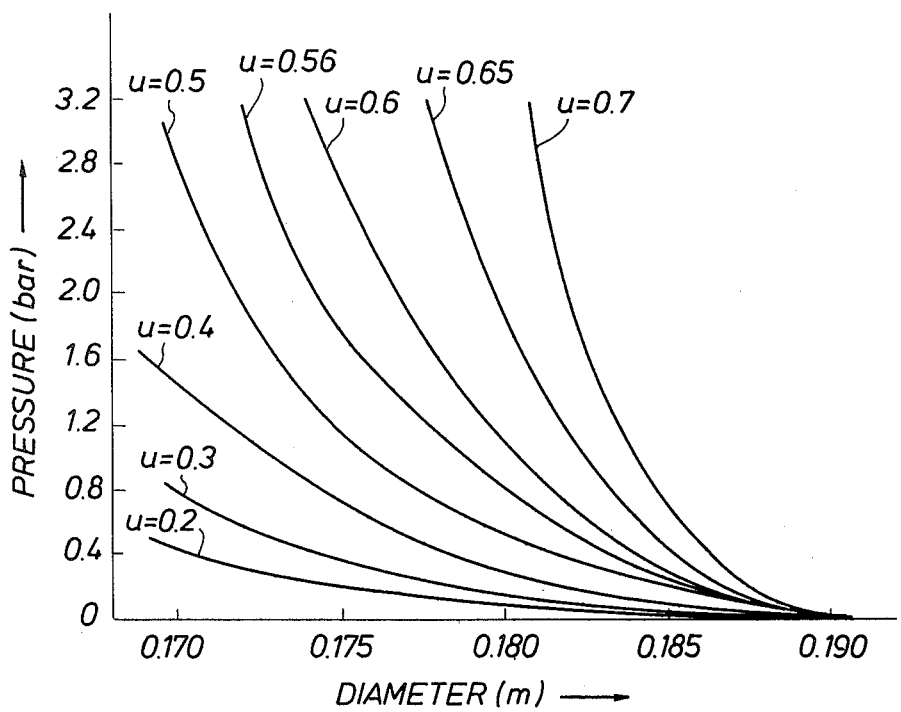
FIG. 5 shows examples of curves, each curve having a different coefficient of friction between pig and internal pipeline wall.

FIG. 5 shows an example of a set of pressure versus diameter curves, each curve representing a different coefficient of friction between pig and internal pipeline wall for a cup-shaped pig.

It will be appreciated that any suitable pig may be used, said pig being propelled through the pipeline in any propelling medium suitable for the purpose. The distance from the inlet in the pipeline may be determined by any means suitable for the purpose, for example a count-wheel or clock means. Examples of such pigs are sphere-shaped pigs, cup-shaped pigs, etc. These pigs are known to those skilled in the art and are not described further in detail. An advantageous embodiment of a pig which may be used according to the method of the invention is an ellipsoidal shaped pig.

It will be appreciated that p average can be taken over intervals of any length suitable for the purpose and that any suitable pipeline distance can be covered.

Further the pump 3 may be any suitable pump, or constant volume source.

It will be appreciated that the pressures can be measured in any suitable way, for example by means of a strain gage transducer. Pressure and flow signals may be recorded on any recording device suitable for the purpose, for example a strip chart recorder, an oscillographic recording device or high speed data logger.

The flow transducer 4 may be any suitable transducer, e.g., an orifice plate or a mass flow meter. Such devices are known to those skilled in the art.

Various modifications of the invention will become apparent to those skilled in the art from the foregoing description and accompanying drawings. Such modifications are intended to fall within the scope of the appended claims.

What is claimed is:

1. A method for determining the variations with time of the internal condition of a pipeline or tubing, comprising propelling a pig, which is sealed against the pipeline or tubing wall, through the pipeline by means of a constant flowing driving fluid; continuously measuring and recording the pressure of the driving fluid during passage of the pig through the pipeline or tubing; deriving from the recorded pressure signals a plurality of quantities representative of the pressure variations in successive intervals of the pipeline or tubing, each interval having a predetermined length to cover the total length of the pipeline or tubing to be inspected; comparing the values of the quantities thus obtained with previously determined reference data of these quantities for the pipeline or tubing being inspected; and deriving from said comparison information as to the internal diameter variations of the pipeline or tubing being inspected.

2. The method as claimed in claim 1, wherein the said previously determined reference data represent a one-to-one correspondence between a set of previous pressure values and a set of previous diameter values of the pipeline or tubing being inspected.

3. The method as claimed in claim 2, wherein the reference data are obtained by determining the diameter data by means of a pig.

4. The method as claimed in claim 1, wherein the pressure differential across the pig is measured.

* * * * *